United States Patent [19]

Orthner

[11] Patent Number: 4,908,314
[45] Date of Patent: Mar. 13, 1990

[54] PROTEIN C ACTIVATOR

[75] Inventor: Carolyn Orthner, Kensington, Md.

[73] Assignee: American National Red Cross, Washington, D.C.

[21] Appl. No.: 69,496

[22] Filed: Jul. 2, 1987

[51] Int. Cl.$^4$ .......................... C12N 9/50; C12N 9/48; C12Q 1/56
[52] U.S. Cl. .................................... 435/219; 435/184; 435/13; 435/212; 435/810; 424/94.64
[58] Field of Search ...................... 435/4, 23, 219, 212, 435/184, 13, 810, 814, 69, 226; 424/94.64

[56] References Cited

PUBLICATIONS

Kisiel et al., Biochem. Biophys. Res. Commun., 143(3): 917–922, Mar. 30, 1987.
Kisiel et al., Biochem., 16(26): 5824–5831 (1977).
Brandt, *Clinics in Laboratory Medicine*, vol. 4, No. 2, W. B. Saunders Company, Philadelphia, Pa., 247–249 (1984).
Kisiel et al., J. Biol. Chem., 262(26): 12607–12613, Sep. 15, 1987.
Martinoli et al., *Thrombosis Research* 43:253–264, 1986.
Klein et al., *Biochemistry* 25:4175–4179, 1986.
Stocker et al., *Behring. Inst. Mitt.* 79:37–47, 1986.

*Primary Examiner*—Esther M. Kepplinger
*Attorney, Agent, or Firm*—Fleit, Jacobson, Cohn, Price, Holman & Stern

[57] ABSTRACT

A protein C activator is purified from the venom of the Southern copperhead snake. The resultant enzyme is a very specific and efficient activator of protein C. The high efficiency and specificity enables the sensitive measurement of functional protein C levels in plasma and other biological fluids. The enzyme is attached to a solid support material and the resultant enzyme reactor is capable of producing activated protein C at a high yield and is stable under the conditions of use.

4 Claims, 1 Drawing Sheet

FIG.1

FLOW CHART FOR THE PURIFICATION OF PROTEIN C ACTIVATOR

VENOM (500mg) + 25.0 ml OF 0.02M IMIDAZOLE-Cl, 0.10 M NaCl
0.01 M p-AMINOBENZAMIDINE, pH 6.5

- DIALYSIS vs ABOVE BUFFER
- SP-SEPHADEX C-50 (1.4×40cm)
- RINSE WITH ABOVE BUFFER @ 25°C

UNADSORBED    ADSORBED

- ELUTE WITH LINEAR GRADIENT OF NaCl
  FROM 0.10 TO 0.60M (300ml TOTAL)
  IN ABOVE BUFFER AT 25°C

PEAK I

- CONCENTRATION BY ULTRAFILTRATION 10-FOLD
- DIALYSIS vs 0.05M TRIS-Cl, 0.15M NaCl, 6M UREA pH 7.5
- S-200 SEPHACRYL (2.5×85cm)
- ELUTE WITH ABOVE BUFFER AT 4°C

PEAK II (OR LEADING EDGE THEREOF)

- CONCENTRATE BY ULTRAFILTRATION 10-FOLD
- G-100 SEPHADEX (2.0×95cm)
  IN 0.05M TRIS-Cl, 0.15M NaCl
  pH 7.5 AT 4°C

PEAK I

PROTEIN C ACTIVATOR

BACKGROUND OF THE INVENTION

1. Technical Field

The present invention is related generally to the field of enzymology. More particularly, the present invention is related to a protein C activator enzyme.

2. State of the Art

Protein C is a trace plasma protein which has been found to be quite important in the regulation of the hemostatic process. However, protein C is an inactive zymogen which must be "activated" in order to perform its biological functions. In vivo, activation of protein C is thought to occur on the surface of endothelial cells lining the blood vessels by a 1:1 stoichiometric complex of thrombin with the cell surface protein thrombomodulin. In vitro, protein C can be activated by this complex as well as several other enzymes such as thrombin, the Factor X-activating protein from the venom of *Vipera russelli* (RVV-X), trypsin and other preparations (Klein et al, Biochem. 25:4175–4179, 1986; Stocker et al, *Behring Inst. Mitt.* 79:37–47, 1986; Martinoli et al, *Thromb. Res.* 43:253,264, 1986). However, these activators are either relatively inefficient and required in large amounts or are relatively nonspecific and catalyze other reactions at an appreciable rate. In addition, some of these proteases may even be neutralized by antiprotease inhibitors present in the plasma.

SUMMARY OF THE INVENTION

It is, therefore, an object of the present invention to provide a novel enzyme which is highly specific and an efficient activator of protein C.

It is a further object of the present invention to provide a method and a kit for determining protein C level in human body sample employing the new enzyme, either in whole or in part, of the present invention.

It is another object of the present invention to provide a method for activating protein C in vitro or in vivo by reacting the native zymogen with the activator of the present invention either in whole or in part.

Other objects and advantages of the present invention will become evident from the Detailed Description of the Invention.

BRIEF DESCRIPTION OF THE DRAWING

FIG. 1 illustrates a flow chart for the purification of protein C activator.

DETAILED DESCRIPTION OF THE INVENTION

The above and various other objects and advantages of the present invention ae achieved by an isolated substantially pure protein C activating enzyme characterized by:

(a) molecular weight of about 37,000 as determined by sodium dodecyl sulfate (SDS) polyacrylamide gel electrophoresis;
(b) isoelectric point (pI) of about 6.3 as determined by chromatofocussing;
(c) $k_{cat}/K_m$ of about $3 \times 10^6 M^{-1} sec^{-1}$; and
(d) uninhibited by EDTA upto 10 mM.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "substantially pure" as used herein means that the enzyme is homogeneous, showing a single band on gel electrophoresis and as pure as can be obtained by the presently known conventional purification techniques.

ISOLATION AND PURIFICATION OF ENZYME

The steps leading to the isolation and purification of the activator enzyme are described in Example I in the form of a flow chart.

The venom employed was from the Southern copperhead snake (*Agkistrodon contortrix contortrix*), although other venoms may also contain this enzyme in which case it may be purified in a similar manner if the overall protein composition of the venom is similar.

The preferred temperature, pH and salinity of the SP-Sephadex chromatography are those as indicated in the flow chart of FIG. 1.

EXAMPLE I

The inclusion of about 6M urea during the S-200 Sephacryl chromatography is essential to affect the desired separation, although approximately the same concentration of other protein denaturants, such as guanidine, may also be employed.

The level of purification of the enzyme obtained by the method of Example I has been quantitated and the isolation and recovery of protein C activator thus achieved is shown in Table 1. The results in Table 1 indicate that the present method results in about 60-fold purification of the enzyme at about a 50% yield.

A comparison between the properties of the activator of the present invention with those of the prior art activators of protein C from Southern copperhead venom is shown in Table 2.

TABLE I

Quantitation of Purification and Recovery of Protein C Activator

| Purification Step | Volume ml | Protein mg/ml | Total Protein mg | PCA Activity units/ml | Total Activity units | Specific Activity units/mg | Fold Purification | Yield % |
|---|---|---|---|---|---|---|---|---|
| Venom | 26 | 22.3 | 580 | 2,144 | 55,744 | 96 | 1 | 100 |
| SP-Sephadex | 36 | 1.1 | 39 | 1,239 | 44,604 | 1,144 | 12 | 80 |
| Sephacryl S200 | 30 | 0.5 | 16 | 1,288 | 38,626 | 2,414 | 25 | 69 |
| Sephadex G100 | 34 | 1.5 | 5 | 9,064 | 30,816 | 6,163 | 64 | 55 |

TABLE II

Comparison of Properties of Activators of Protein C from Southern Copperhead Venom

| Activator | Type | Molecular Weight | pI | Second Order[+] Rate Constant $M^{-1} sec^{-1}$ | Inhibition by EDTA |
|---|---|---|---|---|---|
| Present invention[1] | Serine protease | 37,000 | 6.0 | $3.4 \times 10^6$ | No; up to 10 mM |
| Walker enzyme[2] | Serine protease | 20,000 | N.D. | $4.4 \times 10^5$ | Yes ($k_i$ = 8 mM) |
| Protac ®[3,4] | Non-enzymatic | 39,000 | 3.0 | N.D. | No |

[1]Orthner, C. L., Bhattacharya, P. and Strickland, D. K. (1987) Biochemistry, In preparation
[2]Klein, J. D. and Walker, F. J. (1986) Biochemistry, 25 (15), 4175–4179.
[3]Martinoli, J. L. and Stocker, K. (1986) Thromb. Res. 43, 253–264.
[4]Stocker, K., Fischer, H., Meier, J., Brogli, M. and Svendsen, L. (1986) Behring Inst. Mitt. 79, 37–47.
+ $k_{cat}$/Km of Protein C activation reaction Determination of functional Protein C in Human Body Sample: Human plasma is used to illustrate this method. Microliter amount of plasma (about 10–100 µl) is incubated in a buffer at about neutral pH at about 30° C. in the presence of approximately 5 mM EDTA and concentration of NaCl not to exceed about 0.15M. The reaction is started by the addition of a low concentration of protein C activator, either in whole or in part, and allowed to proceed for a specific time interval. Then, soybean trypsin inhibitor is added which stops the reaction by inhibition of the activator enzyme. After the addition of NaCl to approximately 0.15M and a chromogenic substrate which is relatively sensitive to activated protein C as compared to the residual protein C activator, the rate of amidolysis of substrate is measured and the amount of activated protein C is thus quantitated.

Example II provides a more specific illustration of this assay.

EXAMPLE II

Fresh frozen plasma (50 µl) was incubated at 30° C. in 0.05M Tris-Cl containing 1 mg/ml polyethyleneglycol 8000 and 5.5 mM EDTA at pH 7.5 in a total volume of 180 µl. Protein C activator (20 µl) was added to a final concentration of 92 nM and the mixture was incubated for 10 minutes, at which time 5 µl of 50 mg/ml soybean trypsin inhibitor was added. Following the addition of NaCl to 0.13M and the chromogenic substrate L-pyroglutamyl-L-prolyl-L-arginine-p-nitroanilide to 0.8 mM, and water to a total volume of 300 µl, the rate of amidolysis of substrate was measured spectrophotometrically at 410 nm.

Method for Preparing Activated Protein C: This involves several steps which are as follows: (a) Attachment of the protein C activator, in whole or in part, to a solid material; (b) Incubation of the resultant immobilized enzyme from step (a) with an aqueous solution containing protein C; (c) separation of the immobilized-protein C activator from the solution containing the resultant products of step (b).

Attachment of the protein C activator is accomplished by chemical means using N-hydroxysuccinimide ester-derivatized agarose beads. An example of the solid support material which can be used is chemically-cross linked agarose beads having a nominal particle size of 70–300 microns and a pore size with a nominal exclusion limit of $5 \times 10^6$ daltons (Bio-Gel[R]A-5 m). N-hydroxysuccinimide ester-derivatized beads having a 10 atom-long neutral spacer arm can be obtained commercially as Affi-Gel 10 from Bio-Rad Laboratories.

Various alternate means may also be employed so long as the groups which participate in the chemical linkage of the protein do not affect the integrity of the enzyme. Of course, alternate means of attaching to a solid suppport other than covalent chemical linkage may also be employed. An example of such procedure is high affinity non-covalent binding of the enzyme to specific antibodies, which in turn are chemically cross-linked to the solid support material. It should also be recognized that a process may not involve attachment of the enzyme to a solid support material, but that the activator may be used in solution if a highly efficient and specific means of removing it from the reaction mixture is used at a later step in the process.

Agarose beads which differ in particle size and/or pore size from the above is also a suitable matrix for enzyme immobilization. In addition, the chemical structure of the neutral spacer arm between the agarose bead and the reactive N-hydroxysuccinimide group may vary. Solid phase material other than agarose may also be useful such as chemically-derivatized nitrocellulose or plastic polymers.

Protein C activation is accomplished by incubating immobilized protein C activator with protein C in a suitable container such as a plastic receptacle containing a buffered aqueous solution of about pH 7 and a concentration of NaCl of about 0.02M at a temperature of about 30° C. for periods of time up to about 24 hours. The protein C concentration can range from about 0.01 to 1.0 mg/ml, preferably from 0.04 to 0.4 mg/ml.

The method requires mixing to increase the efficiency of the reaction. This is accomplished using end-over-end rotation on a mechanical rotator. Other suitable reactors include a batch reactor with a mixing means such as a magnetic stirrer or alternatively a fixed bed reactor in column-type configuration under liquid flow conditions.

The final step of the method involves separation of the activator from the products of the reaction. This is preferably accomplished by low-speed centrifugation (approximately 8,000×/g for 5 min.) and aspiration of the resultant supernatant. An alternative method of separation may include filtration using a membrane having an appropriate and narrow range of pore sizes to allow filtration of the protein while retaining the agarose beads.

The above method results in 50–100% conversion of protein C to activated protein C as determined by sodium dodecyl sulphate-polyacrylamide gel electrophoresis as well as by specific activity measurements using chromogenic substrates. The resultant activated protein C has been recovered from the product mixture at >80% yields. When employed as above, the activator is stable for at least 4 months. For re-use the immobilized activator is rinsed between uses with 4M NaCl and stored at 4° C.

The activated protein C as produced by the method of the present invention possesses similar functional properties as known for protein C activated by its presumed physiological activator thrombin. These properties include (1) rapid inactivation of Factor VIIIa at picomolar concentrations of activated protein C in vitro; (2) neutralization of plasminogen activator ihnibitor (PAI) activity in vitro; (3) approximately the same activity of amidolysis of chromogenic substrates.

The method of producing activated protein C is further illustrated by Example III.

EXAMPLE III

The purified activator of the present invention was covalently attached to agarose beads by using Affi Gel 10 obtained commercially from Bio-Rad Laboratories, Richmond, CA. Gel slurry, as obtained from the manufacturer, was removed to a scintered glass funnel and rinsed quickly with about a 5-fold amount of ice cold water and drained to a wet cake under vacuum. The wet cake was transferred to a plastic stoppered receptacle containing 0.2 ml of protein C activator at a protein concentration of 0.5 mg/ml for each ml of original gel slurry. The protein C activator had been equilibrated by dialysis in 0.10M HEPES (N-2-hydroxyethylpiperazine-$N^1$-2-ethanesulfonic acid) buffer, pH 7.5 prior to use. The mixture was incubated at 4° C. for 4 hours, at which time 0.1 ml of 0.1M glycine ethyl ester, pH 8 was added per ml of original slurry and incubation continued for an additional 18 hours. The mixture was removed to a scintered glass funnel and rinsed with 0.05M Tris-Cl, 2M NaCl, pH 7.5, to remove non-covalently bound protein. The resultant protein C activator-coupled gel was stored in 0.05M Tris-Cl, 0.02M NaCl pH 7.5 at 4° C.

Protein C activation by immobilized-protein C activator was performed as follows. A given amount of 50% (by volume) slurry of protein C activator agarose gel was removed to a stoppered plastic container, centrifuged (8000 ×/g, 5 min) and the supernatant aspirated. To the resultant gel was added 2 ml of purified protein C, which had been equilibrated by dialysis against 0.05M Tris-Cl, 0.02M NaCl, pH 7.5, and had a protein concentration of 0.4 mg/ml, for every ml of original slurry. The mixture was incubated at 25° C., with mixing being accomplished by a mechanical rotator (Rugged Rotator, Model RD-250, Kraft Apparatus, Inc., Mineola, NY) at 36 rpm. After 19 hours, the mixture was centrifuged (8000×g, 5 min) and the supernatant containing activated protein C recovered by aspiration.

Since the activator of the present invention is substantially pure and has very high specificity for protein C, the availability of such pure activator now makes it possible to activate protein C in vivo by administering to a recipient an activating amount of the purified activator to activate protein C. About 0.1 to 10 μg of the enzyme per dosage may be sufficient for such purposes, however, a therapeutic dosage and regimen can be easily determined following standard procedures or tests well known in the art.

It may be noted that the enzyme of the present invention has a major advantage over the prior art protein C activator Protac ®. Since the instant activator is a catalyst, it can be removed subsequent to the activation of protein C while Protac ® has a noncatalytic mechanism and is required to be present as part of a macromolecular complex with protein C to exert its activating effect. This limits the usefulness of Protac ® for producing activated protein C for therapeutic use because of the high probability of adverse immunological reactions to this foreign protein if it were administered to the patient to maintain protein C activity.

Two other highly specific protein C activators from the venom of the Southern copperhead snake have been described (Klein et al, and Martinoli et al, supra). Protac ® was found to be a protein having a molecular weight of 37,000 as measured by sodium dodecyl sulphate-polyacrylamide gel electrophoresis in the absence or presence of reducing agents. Its isoelectric point was found to be 3.0 as determined by isoelectric focussing. The activity of Protac ® was not inhibited by diisopropylfluorophosphate, iodoacetamide or ethylenediaminetetraacetate, specific inhibitors of serine, sulphydryl, and metallo-proteases, respectively. Incubation of Protrac ® with protein C did not cause changes in its electrophoretic behavoir as measured by crossed immunoelectrophoresis.

These findings, taken together with the data relating to the activator dose and yield of the activation product, indicate that Protac ® is not a protease but rather exerts its activating effect by forming a stoichiometric complex with protein C.

In addition, Klein et al supra purified a protein C activator, the properties of which are also very different from Protac ®. This activator is also a protein, but has a molecular weight of only 20,000 as measured by sodium dodecyl sulphate-polyacrylamide gel electrophoresis under nonreducing conditions. This same molecular weight was estimated by gel filtration on Superose 6 (Pharmacia). The activity of the activator was inhibited by diisopropylfluorophosphate and soybean trypsin inhibitor which indicated that it was a serine protease. The activator was also inhibited by millimolar concentrations of ethylenediaminetetraacetate (EDTA). Antithrombin III has no effect on its activity. Activation of protein C using this enzyme resulted in cleavage of the heavy chain of protein C as monitored by sodium dodecyl sulphate-polyacrylamide gel electrophoresis.

In contrast, the activator enzyme of the present invention has properties which clearly distinguish it from the prior art activators. The activator of the present invention is a protein which has a molecular weight of 37,000 as determined by sodium dodecyl sulphate-polyacrylamide gel electrophoresis in the presence or absence of reducing agents ruling out the possibility that it is a dimer of the protein described by Klein et al. supra. This molecular weight agreed well with an apparent molecular weight of 39,000 when estimated under nondenaturing conditions by high pressure gel permeation chromatography. Furthermore, the activator of the present invention has an isoelectric point of 6.3 as determined by chromatofocussing which is much higher than the isoelectric point of 3.0 reported for Protac ®. The activity of the activator of the present invention is inhibited by the serine protease inhibitors p-nitrophenyl, p-guanidinobenzoate, phenylmethylsulphonylfluoride, D-Phe-Pro-Arg-chloromethylketone, and soybean trypsin inhibitor. The inhibition constant (Ki) of D-Phe-Pro-Arg-Chloromethylketone was determined to be 34 uM which is approximately 500-fold higher than the Ki of thrombin inhibition by this compound. The second order rate constant of protein C activation by the instant activator as estimated by the $k_{cat}$/Km ratio is $3 \times 10^6 M^{-1} sec^{-1}$, which is approximately 10 to 1000-fold higher than the rate constant found for thrombin, thrombin:thromobomodulin, and the activator reported by Klein et al. Moreover, the instant activator is not inhibited by millimolar concentrations (upto 10 mM) of ethylenediaminetetraacetate. Activation of protein C by the present enzyme resulted in proteolysis of the heavy chain of protein C as analyzed by sodium dodecyl sulphate-polyacrylamide gel electrophoresis (data not shown)

Preparation of a pharmaceutical composition comprising proteolytic amount of the activator of the present invention, either in whole or in part, in a pharmaceutically acceptable, sterile, non-toxic carrier such as physiological saline or buffer and the like to activate protein C now also becomes possible. A kit comprising a container containing the activator of the present invention, which may be lyophilized and/or cryopreserved, and instructions to perform the assay for determining the level of protein C as described herein supra, also now becomes possible. Such additives as the preservatives, sterilants adjuvants and the like well known in the art may also be included.

It is understood, of course, that the examples and embodiments described herein are for illustrative purposes only and that various modifications or changes in light thereof will be suggested to persons skilled in the art and are to be included within the spirit and purview of this application and scope of the appended claims.

What is claimed is:

1. Isolated, substantially pure activator of protein C comprising:
    (a) a molecular weight of about 37,000 as determined by sodium dodecyl sulfate polyacrylamide gel electrophoresis;
    (b) an isoelectric point of about 6.3 as determined by chromatofocussing;
    (c) $k_{cat}/K_m$ of about $3 \times 10^6 M^{-1} sec^{-1}$; and
    (d) uninhibited by EDTA upto 10 mM.

2. A kit for determining the level of protein C in a human body sample, comprising a container containing isolated, substantially pure activator of protein C having a molecular weight of about 37,000 as determined by sodium dodecyl sulfate polyacrylamide gel electrophoresis; isoelectric point of about 6.3 as determined by chromatofocussing; $k_{cat}/K_m$ of about $3 \times 10^6 M^{-1} sec^{-1}$; uninhibited by EDTA upto 10 mM and instructions for performing tests employing said activator.

3. A method for producing active protein C, comprising reacting native protein C in vitro with a proteolytic amount of the activator of claim 1 under proteolytic conditions to produce activated protein C.

4. The method of claim 3 further comprising:
    recovering activated protein C.

* * * * *